(12) United States Patent
Cipriani et al.

(10) Patent No.: US 9,480,857 B2
(45) Date of Patent: Nov. 1, 2016

(54) APPLICATOR FOR APPLYING A RADIOACTIVE SUBSTANCE TO A BIOLOGICAL TISSUE

(75) Inventors: Cesidio Cipriani, Rome (IT); Maria Desantis, Rome (IT); Max Bichlmaier, Hohenlinden (DE); Siegfried Förg, Pastetten (DE); Tuomo Kaarlo Nikula, Ottobrunn (DE); Mark Harfensteller, Unterschleissheim (DE); Oliver Buck, Bayerisch Gmain (DE)

(73) Assignee: ONCOBETA INTERNATIONAL GMBH, Ravensburg (DE)

( * ) Notice: Subject to any disclaimer, the term of this patent is extended or adjusted under 35 U.S.C. 154(b) by 920 days.

(21) Appl. No.: 13/511,614

(22) PCT Filed: Nov. 16, 2010

(86) PCT No.: PCT/EP2010/006971
§ 371 (c)(1),
(2), (4) Date: Aug. 21, 2012

(87) PCT Pub. No.: WO2011/063903
PCT Pub. Date: Jun. 3, 2011

(65) Prior Publication Data
US 2013/0006033 A1     Jan. 3, 2013

(30) Foreign Application Priority Data
Nov. 24, 2009   (DE) .................. 10 2009 054 388

(51) Int. Cl.
*A61N 5/10*          (2006.01)
*G21F 3/00*          (2006.01)

(52) U.S. Cl.
CPC ............... *A61N 5/1001* (2013.01); *A61N 5/10* (2013.01); *A61N 2005/1021* (2013.01); *G21F 3/00* (2013.01)

(58) Field of Classification Search
CPC .... A61N 5/10; A61N 5/1001; A61N 5/1002; A61N 5/1007; A61N 5/1014; A61N 5/1015; A61N 5/1027; A61N 5/1028; A61N 5/1029; A61N 2005/1008; A61N 2005/1019; A61N 2005/1021; A61N 2005/1024; G21F 5/00; G21F 5/002; G21F 5/005; G21F 5/015; G21F 5/014; A61M 5/1785
USPC ........................................................ 600/1–8
See application file for complete search history.

(56) References Cited

U.S. PATENT DOCUMENTS

| | | |
|---|---|---|
| 2,932,974 A | 4/1960 | Kaspaul |
| 4,092,546 A | 5/1978 | Larrabee |

(Continued)

FOREIGN PATENT DOCUMENTS

| | | |
|---|---|---|
| DE | 1 149 134 | 5/1963 |
| DE | 10 2007 006 189 A1 | 8/2008 |
| KR | 2009 0076071 A | 7/2009 |

*Primary Examiner* — Charles A Marmor, II
*Assistant Examiner* — Carrie R Dorna
(74) *Attorney, Agent, or Firm* — Saliwanchik, Lloyd & Eisenschenk

(57) ABSTRACT

An applicator for applying a radioactive substance to a biological tissue, the applicator comprising a container for receiving the radioactive substance; an application device connectable to the container, by which the substance compound can be applied to the tissue; and at least a part of a conveying device by which the radioactive substance can be supplied from the container into the application device when the application device has been connected to the container.

19 Claims, 3 Drawing Sheets

(56) References Cited

U.S. PATENT DOCUMENTS

| | | | |
|---|---|---|---|
| 4,307,713 A | 12/1981 | Galkin et al. | |
| 5,505,712 A | 4/1996 | McMillian | |
| 5,514,071 A * | 5/1996 | Sielaff et al. | 600/3 |
| 5,860,909 A * | 1/1999 | Mick et al. | 600/7 |
| 5,927,351 A | 7/1999 | Zhu et al. | |
| 6,033,377 A | 3/2000 | Rasmussen et al. | |
| 6,586,758 B2 * | 7/2003 | Martin | 250/515.1 |
| 6,767,319 B2 * | 7/2004 | Reilly et al. | 600/5 |
| 2003/0028068 A1 | 2/2003 | Steele, Sr. et al. | |
| 2005/0277833 A1 * | 12/2005 | Williams, Jr. | A61M 5/16827 600/431 |

* cited by examiner

APPLICATOR FOR APPLYING A RADIOACTIVE SUBSTANCE TO A BIOLOGICAL TISSUE

CROSS-REFERENCE TO RELATED APPLICATIONS

This application is the U.S. national stage application of International Patent Application No. PCT/EP2010/006971, filed Nov. 16, 2010, which claims the benefit of German Patent Application No. 10 2009 054 388.0, filed Nov. 24, 2009, the disclosures of which are incorporated by reference herein in their entirety, including any figures, tables, or drawings.

The present invention relates to an applicator for applying a radioactive substance to a biological tissue, specifically the human skin, for medical purposes as well as to a handle suited thereto, and an appropriate application system.

In nuclear medicine, radioactive substances are used for the treatment of near-surface parts of a tissue such as those of the skin. The radioactive substance, which is often applied to the skin as a constituent of a cream or lacquer, destroys near-surface cells in dependence on the penetration depth and exposure time of the radioactive radiation. This method can be used for the therapy of basal cell carcinomas, for example, and resulted in successful treatments.

The application of the radioactive substance to the skin parts to be treated has been done in a liquid form, as a mixture of substances included in a cream or lacquer or as a radioactive substance included in a plaster.

The problem of this method is, however, that the treatment of the near-surface parts of a tissue is done without any appropriate aids so that the medical personnel are exposed to a high radiation dose, at least when they apply the radioactive substance and remove it from the surface of the skin. In addition, persons preparing the creams, lacquers or plasters which include the radioactive substance are also exposed to a high radiation dose.

It is the object of the present invention to provide a device by which a radioactive substance for the medical treatment of biological tissue, specifically the skin, can be applied thereto while reducing the radiation exposure for persons performing the treatment, as well as an appropriate system.

This object is accomplished by an applicator for applying a radioactive substance to a biological tissue, which comprises a container for receiving the radioactive substance; an application device connectable to the container, by which the substance compound can be applied to the tissue; and at least a part of a conveying device by which the radioactive substance can be supplied from the container into the application device when the application device has been connected to the container. This object is also accomplished by a handle for holding the applicator, which comprises a receiving device for the applicator; at least one driving device, which can be coupled to the conveying device of the applicator, for supplying the radioactive substance into the application device; and a shielding device for providing shielding from radioactive radiation, specifically for protecting the hand which holds the handle.

The applicator according to the present invention for applying a radioactive substance to a biological tissue comprises a container for receiving the radioactive substance; an application device connectable to the container, by which the substance compound can be applied to the tissue; and at least a part of a conveying device by which the radioactive substance can be supplied from the container into the application device when the application device has been connected to the container.

The applicator according to the present invention allows to transport and to store in the container of the applicator during a period prior to the treatment an amount of a mixture of substances prepared and metered in advance which includes a radioactive substance for the treatment of a biological tissue, and to directly apply it to a biological tissue such as the human skin by means of the application device within the applicator. As the mixture of substances provided in the container can be produced prior to use in an automated manner as appropriate and can be measured in terms of the desired radiation dose, the treatment can be carried out easily without needing to carry out any additional preparatory steps. Immediately before the application, it is only necessary to connect the application device to the container of the applicator prepared for a patient. The conveying device helps to precisely dose the mixture of substances into the application device and onto the tissue. The conveying device may be, for example, a piston or plunger which is sealed against the walls of the container and is pushed into the container manually or by means of a drive. The conveying device can be designed as a manually operated piston or plunger.

A further advantage of the applicator according to the present invention is that the applicator can be designed as a throw-away article provided for the individual treatment, a specific amount of a mixture of substances being provided in the container for a patient and the applicator being completely disposed of after the treatment so that any contamination of persons or cleaning devices can be avoided.

According to a preferred embodiment, the container comprises an aperture for connecting the application device to the container, and a cover by which the aperture can be closed. The cover is used to separate the container from the application device prior to use and to prevent the radioactive substance from entering the application device. To improve the shielding of the environment against radioactive radiation caused by the active substance, it is conceivable to manufacture the container from a shielding material such as tungsten or to enclose it with a shielding casing or encasement which may be removable if required.

According to a further embodiment, the applicator has a storage condition in which the container and the application device are fastened to each other, a supply of the active substance or radioactive substance from the container into the application device being prevented by the cover arranged between the application device and the container. According to this embodiment, the applicator may be provided as a device specific to a patient or treatment which is intended for single use, and it can be made ready for use by connecting the application device to the container by removing the cover. The cover may be, for example, a sealing element, specifically a seal, a septum or. any other cover, which can be perforated by pushing the application device into the container.

According to a further embodiment, the application device includes a duct which can be inserted into the container to make the connection in order to be able to supply the radioactive substance to the application device after the connection has been made. The duct may be a capillary tube, a needle or a tubule which can be pressed or pushed by the cover into the container. Alternatively, it is also conceivable to remove the cover before the duct is inserted into the container.

According to a further preferred embodiment, the application device is a brush, a spatula, a sponge, a tubule, a sieve or a needle by which the radioactive substance can be applied to the biological tissue. The suitability of one or more of the above-mentioned application devices for applying a specific mixture of substances including a radioactive substance may depend on the radioactive substance used, its viscosity, the radioactivity used for the treatment, or the type of the tissue to be treated.

According to a further preferred embodiment, the applicator and specifically the container include at least one component of a mixing device. The mixing device may be, for example, a magnetic mixing device which includes a mixing body arranged within the container which can be coupled, by means of magnetic coupling, to a mixing or stirring device arranged outside the container or applicator. The mixing device provided within the container may be, for example, one or more magnetizable beads, rotors or differently formed components which are moved through the container by means of the magnetic coupling to the mixing device.

According to a further preferred embodiment, the container has the form of a tubule. The application device is arranged at, and fastened to, one end of the tubule and forms a continuation of the tubule. According to this embodiment, the applicator therefore has, as a whole, an elongated form or rod form. The application device may be directly fastened to the tubule. Alternatively, a connecting piece may also be used between the application device and the container. If the container has the form of a tubule, the mixing device provided therein may have the form of a metallic, magnetizable component having the form of a cylinder, whose outside diameter is substantially equal to the inside diameter of the tubule.

The application device may be additionally provided with a cap. At its end facing the tubule, the application device may further comprise a tubular portion which is positively and slidably held in a portion of the tubule or connecting piece. The application device can thereby be pushed into the tubule, the cover arranged between the application device and the tubule being penetrated and a connection between the application device and the tubule being made. Alternatively, the application device may also be movably arranged within a connecting piece, the connecting piece being attached on the tubule and including the cover.

In addition, the applicator may be designed in such a way that when the application device is in the storage condition, i. e. in a condition in which it is separated from the container, it is in a first locking position, and when it is pushed into the tubule, it enters a second locking position. Moreover, the applicator may be configured in such a way that the application device, after it had been inserted into the container, can not be reset into the original storage condition to prevent the mixture of substances including the radioactive substance from escaping.

According to the present invention, a handle for holding the applicator is also provided. The handle includes a receiving device for the applicator; at least one driving device, which can be coupled to the conveying device of the applicator, for supplying the radioactive substance into the application device; and a shielding device for providing shielding from radioactive radiation, specifically for protecting the hand which holds the handle.

The handle according to the present invention can be reused with a plurality of applicators having the same configuration or a plurality of similar applicators for the individual treatment of patients. The use of the handle according to the present invention with the shielding device arranged thereon can efficiently protect any person who carries out the treatment against the radioactive radiation of the radioactive substance used for the treatment. In addition, the handle allows the radioactive substance to be precisely dosed or applied to a biological tissue to be treated.

According to a preferred embodiment, the receiving device is made up of a chucking device which can detachably hold the applicator. Preferably, the applicator is inserted into the handle in such a way that the container of the applicator is held or grasped by the chucking device of the handle, whereas the application device of the applicator is directed away from the handle to the front. The handle allows applicators to be grasped with the hand protected by the shielding device of the handle and allows them to be detached from the handle after a treatment has been carried out, without needing to grasp the applicator with the hand.

According to a further preferred embodiment, the driving device of the handle includes an advance mechanism which can apply a thrust force to the conveying device of the applicator. The driving device and the advance mechanism allow the radioactive substance provided in the container of the applicator to be supplied into the application device and to be applied to the tissue to be treated while being dosed precisely. The conveying device may specifically be a piston or a plunger which is received in the container. The advance mechanism is preferably arranged on the handle in such a way that an applicator held in the chucking device is held in such a way that a coupling between its conveying device and the advance mechanism can be made.

According to a further preferred embodiment, the handle includes a separate handheld device on which the advance mechanism is arranged; and a guide wire arranged on the handle, which can be coupled to the conveying device of the applicator and is connected to the advance mechanism. According to this embodiment, the treatment is carried out by means of a two-piece device, the dosing of the amount supplied into the application device being performed by means of the handheld device using one hand, whereas the handle including the applicator being held with the other hand.

According to a further preferred embodiment, the handle has an elongated form, the receiving device for the applicator being arranged on one end and the handle having a duct in its interior for receiving the guide wire. The duct extends through the handle in its longitudinal direction up to the application device so that the and of the guide wire can be coupled to the applicator or to its conveying device.

According to a further embodiment, a part of the receiving device comprises a shielding which covers a part of the applicator received in the receiving device. Preferably, the container of the applicator, which has been received in the receiving device and which contains the radioactive substance, is shielded by a shielding of the handle, which encloses the receiving device.

According to the present invention, a system is provided which includes a handle according to the present invention and a transfer container for storing one or more of the applicators according to the present invention.

According to a preferred embodiment, the transfer container includes a component of a magnetic mixing device which can be coupled, by magnetic coupling, to a further component of the mixing device which is arranged within the applicator. In addition, the transfer container can be designed in such a way that only one applicator at a time can be taken out of it. To that end, an appropriate locking mechanism can be provided on the transfer container.

According to a further preferred embodiment, the system includes a frame on which the transfer container and a fixture for the handle are movably arranged so that the handle arranged in the fixture can be moved towards the transfer container for taking out an applicator stored therein. In this way, an applicator can be taken with the handle without needing to grasp the handle with the hand. This allows the radiation dose to be further reduced to which persons are exposed who operate the handle. The frame can be designed in a mobile manner.

According to a further embodiment, the system includes a measuring unit for measuring the radioactivity applied to the biological tissue; and a shielded waste bin. The measuring unit may be, for example, an alpha, beta or gamma detector such as a scintillation detector or a calibrator, which is used to measure, prior to and after the application to the biological tissue, the activity of the radioactive substance contained within the applicator and to determine, from the difference between the activities in the applicator, the activity of the radioactive substance applied. However, the activity of the radioactive substance applied to the biological tissue can also be determined by measuring, specifically optically measuring, using an appropriate measuring head that area of the biological tissue to which the radioactive substance was applied and by measuring the area activity, i. e. the activity per unit area.

According to a further preferred embodiment, the waste bin and the measuring unit are movably arranged on the frame so that the handle arranged within the fixture can be moved towards the waste bin for taking up an applicator or for measuring the radioactivity of an applicator.

According to a preferred embodiment, the transfer container, the measuring unit and the waste bin are rotatably arranged on a rotary table, for example, whereas the fixture is linearly movably arranged above the rotary table so that a handle held within the fixture can be lowered into the transfer container, measuring unit and waste bin to take up an applicator, to measure the radioactive radiation originating from it or to put down the applicator.

Further properties, features and advantages of the invention will appear from the description of an exemplary embodiment in conjunction with the accompanying drawings, in which.

Figure 1A:
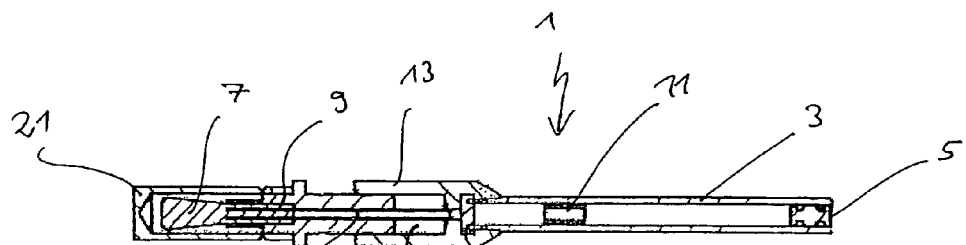
FIGS. 1a and 1b show a schematic representation as a sectional view of the applicator of the present invention according to an embodiment in a storage condition (FIG. 1a) and in a use condition (FIG. 1b)

In the following, the applicator 1 of the present invention, the handle of the present invention and the application system will be described with reference to an exemplary embodiment represented in FIGS. 1 to 5. According to the embodiment described, the applicator 1 is a carpule system having a body formed as a tubular container 3, for receiving an active ingredient material or active ingredient compound which includes a radioactive substance for a medical treatment of a biological tissue such as the skin, for example. The active ingredient material or active ingredient compound may comprise any combination suited for the treatment of a tissue, of one or more radioactive substances such as rhenium, and additives. The active ingredient material or active ingredient compound may be present in a liquid form, as a cream or lacquer or as a suspension.

One end of the applicator 1 is sealed with a movable and sealing cylindrical piston or plunger 5, e. g. a cylindrical solid or hollow metallic component having integrated O-rings. The plunger 5 is arranged within the container 3 in such a way that the active ingredient compound is pressed from the container 3 into an application device 9 of the applicator 1, which is provided with a brush 7, by exerting a pressure on the outwardly oriented side of the plunger 5. The plunger 5 can be mounted in the container 3 before the active ingredient compound is filled in.

For a thorough mixing of the active ingredient compound, a mixing member 11 is provided within the container 3, which is made of a magnetizable material and can be reciprocated within the body by means of magnetic forces which are generated by a mixing or stirring device arranged outside of the body. After the container 3 has been filled with the active ingredient compound, the front portion of the container 3 is closed with a connecting piece 13 which, similarly to the container 3, has a tubular form having an inside diameter which corresponds to the outside diameter of the container 3. A seal 15 is integrated into the connecting piece 13 to prevent the active ingredient compound from leaking during transport and storage. That side of the connecting piece 13 which is opposite to the side serving as a cover is formed as a cylindrical receptacle 17 having an inside diameter in such a way that the application device 9 can be received therein in a precisely fitting manner. In addition, the receptacle 17 is designed in such a way that the application device 9 is retained in one of two locking positions. In the first locking position shown in FIG. 1a, the application device 9 is in the transport and storage position in which a capillary tube 19 integrated into the brush 7 of the application device 9 does not perforate the seal 15. If the applicator 1 is actuated for use, the application device 9 is pushed into the second locking position shown in FIG. 1b. The applicator 1 is designed in such a way that, in the second locking position, the brush 7 can not be moved back into the first locking position to avoid any contamination. In addition, in the second locking position, the seal 15 is penetrated by the capillary tube 19 so that the active ingredient can be supplied into the brush 7 for application.

The brush 7 is used for applying the active ingredient compound to the surface of the tissue and for distributing it thereon. It is preferably designed as a brush having bristles or hairs but it may also be replaced with another suitable device such as a spatula, blade or a sieve grid made of an elastic plastic or any other suitable material. The brush 7 is protected by a cover 21 which is only removed for applying the active ingredient compound.

Figure 1B:
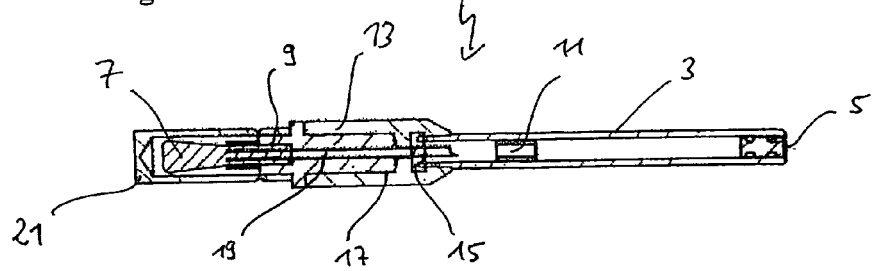
Figure 2:
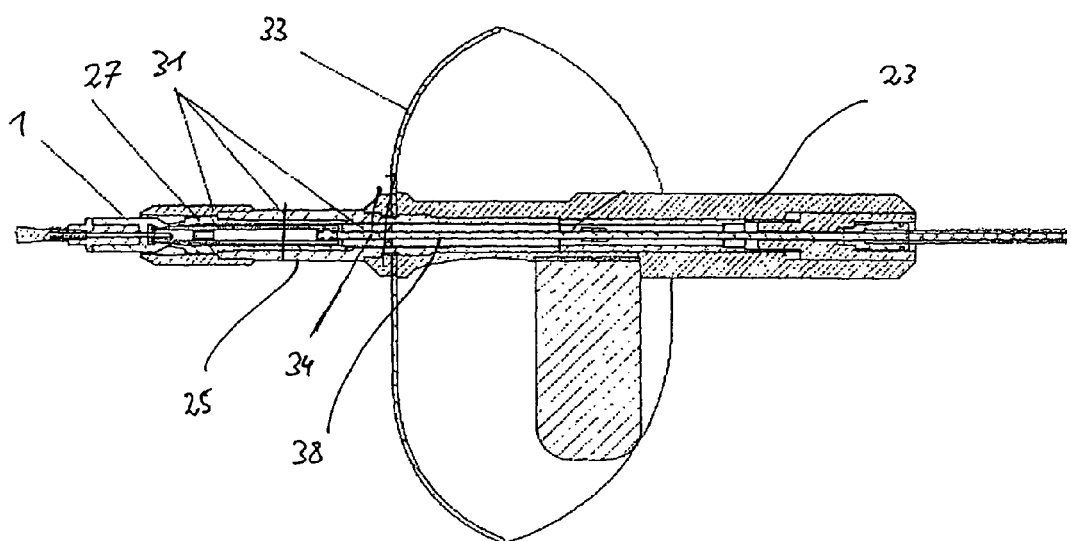
FIG. 2 shows a handle of the present invention for use with the applicator of the present invention according to the embodiment shown in FIGS. 1a, 1b in a sectional view.
Figure 3:
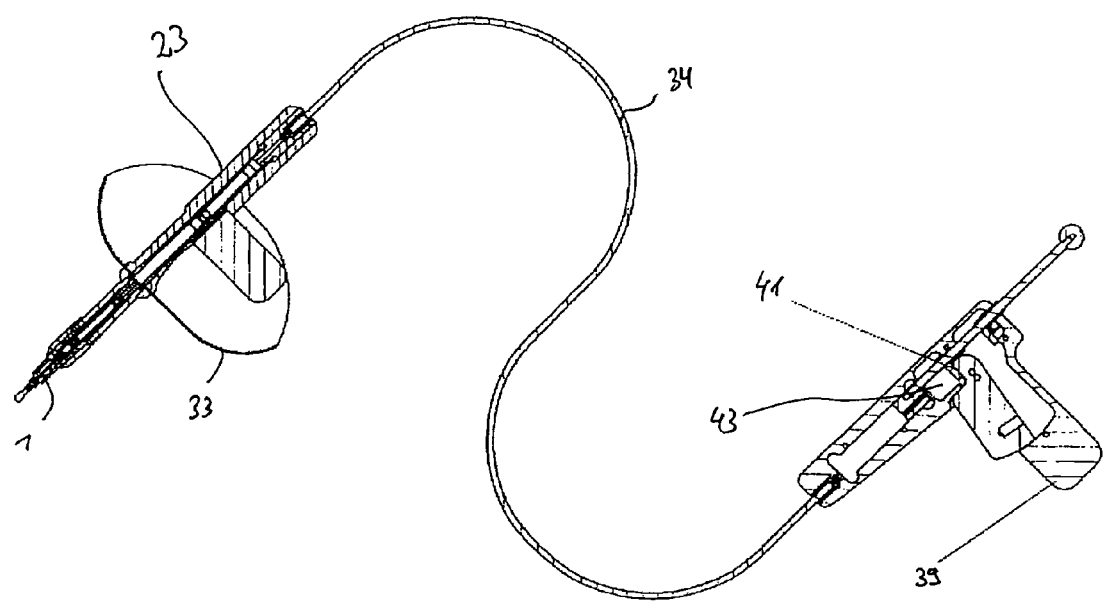
FIG. 3 shows, in a sectional view, the handle of the present invention according to the embodiment shown in FIG. 2, and a handheld device according to a preferred embodiment which can be used with the handle.

After the application, the cover 21 is placed again on the brush 7 to prevent a contamination by the brush 7 wetted with the active ingredient compound. The mixing member 11 is designed in such a way that the active ingredient compound can be discharged as completely as possible from the applicator 11 or the carpule. In the present example, the mixing member 11 has a cylindrical form having a central hole. The diameter of the hole is adapted to the diameter of the capillary tube 19 so that the capillary tube 19 fills the dead volume of the hole as completely as possible when the capillary tube 19 is inserted into the container 3 as is shown in FIG. 1b. In addition, the mixing member 11 is designed in such a way that it is prevented from tilting during the mixing or discharging process. The container 3, the application device 9 and the connecting piece 13 may be made of plastic or glass or a combination thereof.

The system further includes a special handle 23 which is designed in such a way that the applicator 1 can be received therein. Using the handle 23 and an applicator 1 held thereon, the active ingredient can be applied to a biological tissue with a high precision and exact dosage. A tip 25 of the generally rod-shaped handle 23, which is arranged for receiving the applicator 1, is designed in such a way that it can be inserted into an appropriate measuring system, preferably a measuring station 26 having a calibrator for determining the activity of the active ingredient within the applicator 1. The handle 23 comprises a mechanism for taking up the applicator 1, which is formed by a chucking mechanism, preferably in the form of a three-piece collet chuck 27. The collet chuck 27 is unlocked by a mechanism within a special loading station 29 shown in FIG. 5 and can be opened only within the loading station 29 for receiving or releasing the applicator 1. The front portion of the handle 23 includes a shielding 31, preferably made of tungsten, to shield the radiation originating from the active ingredient contained in the applicator 1. To shield the hand, the handle 23 also includes a safety shield 33 made of an aluminum alloy, for example. The safety shield 33 has the form of a partial cylinder and is formed so as not to impair the application of the active ingredient compound.

The active ingredient is discharged from the applicator 1 by causing a guide wire 34, which is guided within a duct 38 extending through the handle 23 and is in contact with the plunger 5 of the applicator 1, to move the plunger 5 in the direction of the brush 7. The guide wire 37 is operated through a handheld device 39 held with one hand of a user, whereas the handle 23 is held with the other hand. By means of a lever 41 on the handheld device 39, the guide wire 37 is pushed, with an appropriate reduction of the movement speed, in the direction of the applicator 1 by a mechanism 43 included in the handheld device 39. As an alternative to the handheld device 39, a mechanism for performing the feeding movement can be integrated into the handle 23 itself to allow single hand operation.

Figure 4:
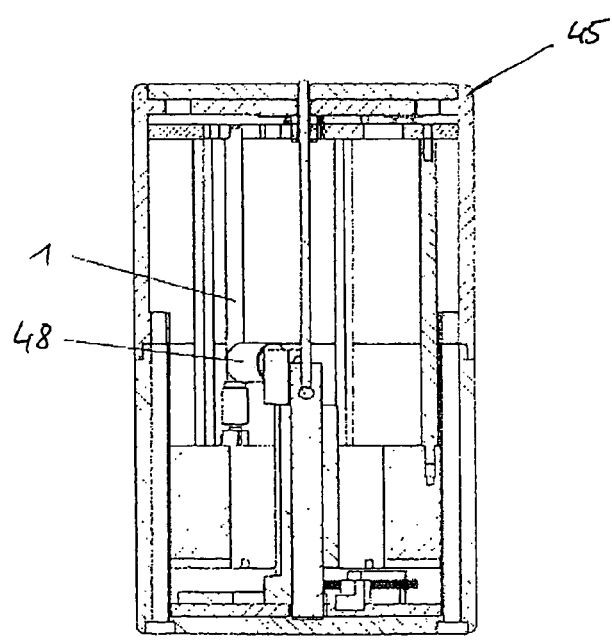
FIG. 4 shows a transfer container for receiving and storing a plurality of applicators of the present invention according to the embodiment shown in FIGS. 1a, 1b in a sectional view.

The cylindrical transfer container 45 shown in FIG. 4 is used for receiving and storing a plurality of, preferably six, applicators 1 or carpules which are received and held in the transfer container 45, preferably upright and in a circular arrangement. For reasons of radiation protection, a locking mechanism 47 of the transfer container 45 ensures that only one applicator 1 can be taken out at a time. In addition, a mechanism is provided in the transfer container 45 which ensures that the respective applicator 1 can not be taken out until mixing has been finished. To that end, a stirring device having a movable magnet 48 is integrated into the transfer container 45, which is used to move the mixing member 11 of the applicator 1 for thoroughly mixing the active ingredient.

Figure 5:
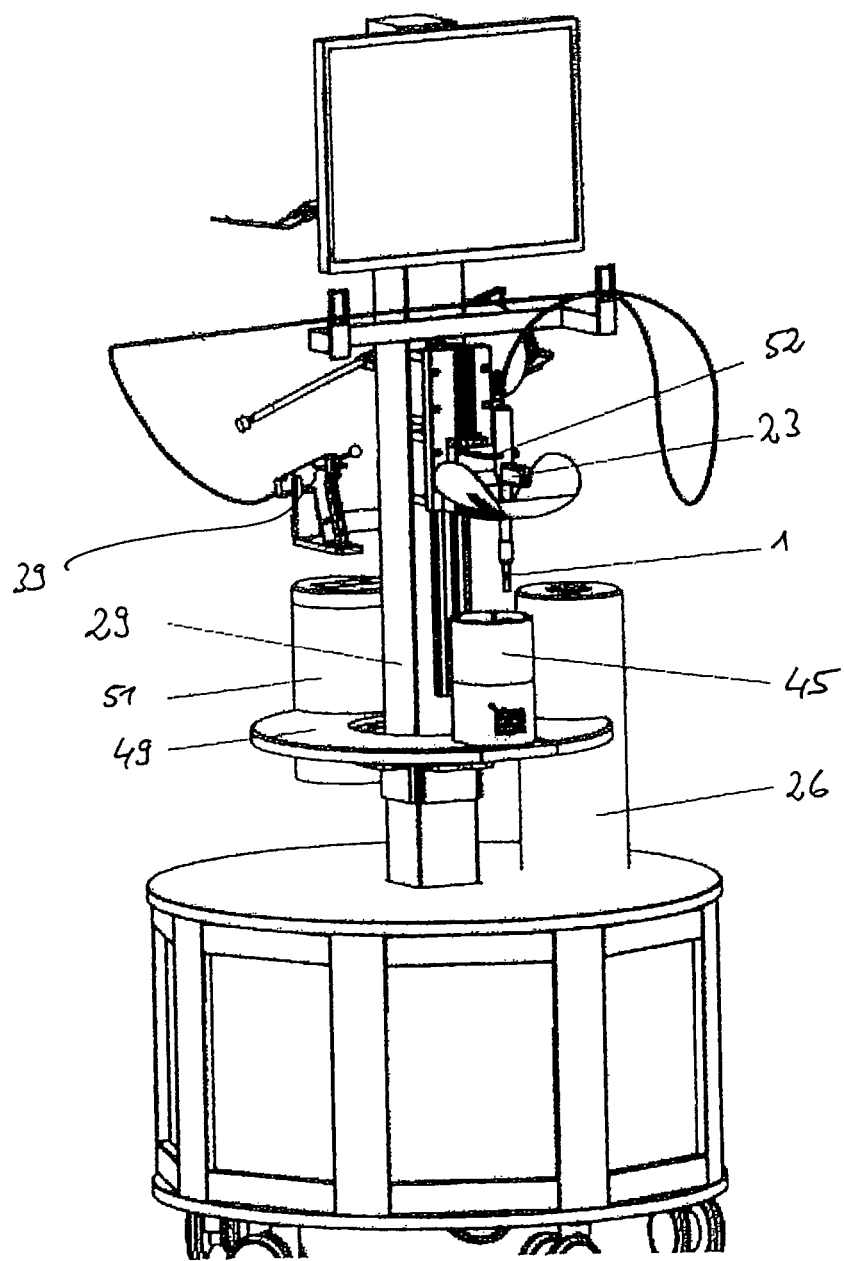
FIG. 5 shows an application system according to an embodiment of the invention in a three-dimensional view.

FIG. 5 shows an example of an embodiment of a mobile application system. The application system includes a frame including the loading station 29 which represents the central unit of the exemplarily shown application system and to which further components are attached. The application system further includes a rotatable unit which is exemplarily shown as a rotary table 49. A receptacle for the transfer container 45, a receptacle for the measuring station 26 and a receptacle for a waste bin 51 are arranged on the rotatable unit. To ensure a collision-free movement of the rotary table 49, a fixture 52 for the handle 23 is arranged at an appropriate distance above the rotary table 49 at the loading station 29. The fixture 52 has a linear degree of freedom in the vertical direction so that the handle 23 received in the fixture 52 can be lowered into the transfer container 45, the measuring station 26 and the waste bin 51 for receiving, measuring and releasing the applicator 1, respectively.

The measuring station 26 includes, as a part of a suitable measuring system, a calibrator which is also referred to as activimeter or well-type ionization chamber and in which the tip of the handle 23 and the applicator 1 can be received. By means of the calibrator, the activity of the active substance within the applicator 1 is determined prior to and after the application.

In addition to the measurement of the activity using the calibrator, the activity of an active substance can also be directly measured on the patient by means of a collimated measuring head in conjunction with an optical measurement of the area of the layer of the active substance applied to the patient. Both of the methods for measuring the activity can be used alternatively or together.

The waste bin 51 serves for receiving the used applicator 1 and can also be used for receiving an active substance which was removed from the tissue after the application. The waste bin 51 has a sufficient shielding which is preferably provided by a layer of a material having a high hydrogen content such as polymethyl methacrylate, for example, to provide shielding from beta rays, and by a layer of a material having a high content of electrons such as tungsten or lead, for example, to trap gamma rays and to provide shielding from them. In this case, the layer of the material having a high hydrogen content is arranged more inside than, and in front of, the layer of the material having a high content of electrons to provide also shielding from the bremsstrahlung of alpha particles which originates at the layer of the material having a high hydrogen content. The cover of the waste bin 51 can be operated through a mechanism. When the waste bin 51 is opened, a gate is exposed into which the handle 23 is inserted to dispose of the used applicator 1. At the same time, an additional aperture is opened to receive the active substance which has been used during the treatment and might have been removed from the tissue spot using an adhesive tape.

In addition to the components described above, the exemplarily disclosed application system also includes tools for removing the active substance from the tissue spots treated. Hereafter, a procedure for applying an active substance including a radioactive substance to a biological tissue such as the skin will be described exemplarily. The exemplary process is divided into four sections which include the preparation and packaging or filling of the active substance, the application of the active substance, the action of the active substance during a period of action and the removal and disposal of the active substance. The active ingredient compound may be a cream, liquid or lacquer including a radioactive substance.

After the active substance has been prepared and has been filled into the container 3 of the applicator 1, the filled applicator 1 is inserted into the transfer container 45. To that end, the mechanism of the transfer container 45 is unlocked to load the transfer container 45 with up to six applicators 1. The locking mechanism 47 is then re-activated to prevent the applicators 1 from being taken out by unauthorized persons. The transfer container 45 is inserted into the loading station 29. The following process steps are restraint-guided to reliably keep to the correct order. The handle 23 is fastened to the fixture 52 at the loading station 29 to unlock the collet chuck 27. Before a new applicator 1 can be loaded into the handle 23, the mixing mechanism at the transfer container 45 has to be actuated. Now the handle 23 with the collet chuck 27 opened is linearly moved into the transfer container 45. In the lowermost position, the collet chuck 27 is closed and the applicator 1 is fastened to the handle 23. The handle 23 is moved out of the transfer container 45 linearly upwards. The rotatable unit 49 at the loading station 29 is continued to be rotated in such a way that the handle 23 is above the measuring station 26. Now the handle 23 is lowered into the measuring station 26 in the same way and the activity within the received applicator 1 is determined. Following this step, the applicator 1 is activated by pushing the capillary tube 19 through the seal 15. In this way, the brush of the capillary tube 19 is moved from the first locking position into the second locking position. In addition, the cover 21 of the brush 7 is removed.

The application of the active ingredient compound may start in the next operating section. To that end, a pumping movement performed at the handheld device 39 causes the guide wire 37 to move the plunger 5 in small steps so that the active ingredient compound flows through the capillary tube 19 into the brush 7. The brush 7 uniformly and thinly distributes the active ingredient compound on the surface of the tissue. Following the application, the activity of the active ingredient compound remaining in the applicator 1 is to be determined. To that end, the handle 23 is moved back to the receptacle of the loading station 29. The handle 23 is lowered into the measuring station 26 to determine the residual activity. When the handle 23 is lowered into the measuring station 26, a new cover is placed on the brush 7 to avoid a contamination. Following the measurement, the rotatable unit 49 of the loading station 29 is continued to be moved in such a way that the handle 23 is above the waste bin 51. By moving the handle 23 into the waste bin 51, the collet chuck 27 of the handle 23 can be unlocked again to dispose of the used applicator 1 into the waste bin 51.

The active ingredient compound has to remain on the tissue for a precisely determined period of time to emit the radiation dose calculated. No operations are performed in this step. During the period of action, the active ingredient compound hardens or dries out After the end of the period of action, the active ingredient compound, which is solid now, has to be removed in the last process step. This may be done, for example, using an adhesive tape attached to an appropriate tool, Subsequently, the surface of the tissue is checked for contamination using an appropriate measuring instrument. If a contamination is determined, the entire last process step has to be repeated.

Numerous modifications can be made to the applicator 1, handle 23 and application system according to the present invention without departing from the scope of the invention.

LIST OF REFERENCE SYMBOLS

1 Applicator
3 Container
5 Plunger
7 Brush
9 Application device
11 Mixing member
13 Connecting piece
15 Seal
17 Cylindrical receptacle
19 Capillary tube
21 Cover
23 Handle
25 Tip
26 Measuring station
27 Collet chuck
29 Loading station
31 Shielding
33 Safety shield
34 Guide wire
38 Duct
39 Handheld device
41 Lever
43 Mechanism
45 Transfer container
47 Locking mechanism
48 Magnet
49 Rotary table
51 Waste bin
52 Fixture

The invention claimed is:

1. An applicator for applying a radioactive substance to a tissue, comprising:
   a container,
   wherein the container is configured to receive a radioactive substance; and
   an application device connectable to the container, wherein the application device and the container are movable with respect to each other between at least two positions,
   wherein the application device is configured to apply the radioactive substance to a biological tissue,
   wherein the container comprises:
      at least a part of a conveying device,
      wherein the at least a part of the conveying device is a piston, and
      wherein the piston is configured to supply the radioactive substance from the container into the application device when the application device is connected to the container,
   wherein the applicator has a storage condition in which the container and the application device are fastened to each other in a first position of the at least two positions, and a supply of the radioactive substance from the container into the application device is prevented by a cover arranged between the application device and the container, and
   wherein the application device is configured to apply the radioactive substance to the biological tissue after the application device and the container have been moved with respect to each other into a second position of the at least two positions in which the supply of the radioactive substance from the container into the application device is no longer prevented.

2. The applicator according to claim 1,
   wherein the container comprises:
      an aperture for connecting the application device to the container, and
   wherein the cover is configured to selectively close the aperture.

3. The applicator according to claim 1,
   wherein the application device comprises:
      a duct,
      wherein the duct is configured to be inserted into the container to make a connection between the application device and the container so that the radioactive substance can be supplied from the container to the application device via the duct after the connection between the application device and the container has been made.

4. The applicator according to claim 1, wherein the application device comprises:
an element selected from the group consisting of:
a brush, a spatula, a sponge, a tubule, and a needle, wherein the element is configured to apply the radioactive substance to the biological tissue.

5. The applicator according to claim 1, wherein the container comprises:
at least one component of a mixing device.

6. The applicator according to claim 1, wherein the container has a form of a tubule and the application device is arranged at one end of the tubule.

7. A handle for holding an applicator comprising:
a receiving device,
wherein the receiving device is configured to receive an applicator,
wherein the applicator comprises:
a container,
wherein the container is configured to receive a radioactive substance; and
an application device connectable to the container,
wherein the application device is configured to apply the radioactive substance to a biological tissue;
at least a part of a conveying device,
wherein the at least a part of the conveying device is configured to supply the radioactive substance from the container into the application device when the application device is connected to the container,
wherein the applicator has a storage condition in which the container and the application device are fastened to each other, and
wherein when the applicator is in the storage condition a supply of the radioactive substance from the container into the application device is prevented by a cover arranged between the application device and the container;
a separate handheld device for operating a guide wire,
wherein the guide wire is guided within a duct of the handle, and
wherein by operating the guide wire a thrust force can be applied to the at least a part of the conveying device of the applicator, for supplying the radioactive substance from the container into the application device; and
a shielding device,
wherein the shielding device provides shielding from radioactive radiation to protect a hand which holds the handle.

8. A system, comprising:
a handle, wherein the handle comprises:
a receiving device,
wherein the receiving device is configured to receive an applicator,
wherein the applicator comprises:
a container,
wherein the container is configured to receive a radioactive substance; and
an application device connectable to the container,
wherein the application device is configured to apply the radioactive substance to a biological tissue; and
at least a part of a conveying device,
wherein the at least a part of the conveying device is configured to supply the radioactive substance from the container into the application device when the application device is connected to the container;
at least a part of a driving device which can be coupled to the at least a part of the conveying device of the applicator,
wherein the at least a part of the driving device coupled to the at least a part of the conveying device is configured to supply the radioactive substance from the container into the application device when the application device is connected to the container; and
a transfer container,
wherein the transfer container is configured to store one or more applicators; and
a frame,
wherein the transfer container and a fixture for the handle are movably arranged on the frame so that the handle arranged in the fixture can be moved towards the transfer container for taking out an applicator of the one or more applicators stored therein.

9. The system according to claim 8,
wherein the transfer container comprises:
a component of a magnetic mixing device,
wherein the component of the magnetic mixing device is configured to be coupled, by magnetic coupling, to a further component of the mixing device, and
wherein the further component of the mixing device is arranged within the applicator.

10. The system according to claim 8,
wherein the system further comprises:
a measuring unit,
wherein the measuring unit is configured to measure the radioactivity of an applicator received in the receiving device.

11. The system according to claim 8,
wherein the system further comprises:
a shielded waste bin.

12. The system according to claim 8,
wherein the system further comprises
a shielded waste bin,
wherein the shielded waste bin is movably arranged on the frame so that the handle arranged within the fixture can be moved towards the shielded waste bin for putting down an applicator received in the receiving device.

13. The system according to claim 10,
wherein the measuring unit is movably arranged on the frame so that the handle arranged within the fixture can be moved towards the measuring unit for measuring the radioactivity of an applicator received in the receiving device.

14. An applicator assembly, comprising:
an applicator,
wherein the applicator comprises:
a container,
wherein the container is configured to receive a radioactive substance; and
an application device connectable to the container,
wherein the application device is configured to apply the radioactive substance to a biological tissue, and
wherein the container comprises:
at least a part of a conveying device,
wherein the at least a part of the conveying device is a piston, and wherein the piston is configured to supply the radioactive substance from the container into the application device when the application device is connected to the container, wherein the applicator has a storage condition in which the container and the application device are fastened to each other, wherein when the applicator is in the storage condition a supply of the radioactive substance from the container into the application device is prevented by a cover arranged between the application device and the container, and wherein the application device is configured to apply the radioactive substance to the biological tissue when the container and the application device are fastened to each other;

a handle, wherein the handle comprises:
 a receiving device,
 wherein the receiving device is configured to receive the applicator; and
 at least a part of a driving device which can be coupled to the at least a part of the conveying device of the applicator,
 wherein the at least a part of the driving device coupled to the at least a part of the conveying device is configured to supply the radioactive substance from the container into the application device; and a shielding device, wherein the shielding device provides shielding from radioactive radiation to protect a hand which holds the handle.

15. The applicator assembly according to claim 14,
wherein the receiving device is formed by a chucking device, and
wherein the receiving device formed by the chucking device is configured to detachably hold the applicator.

16. The applicator assembly according to claim 14,
wherein the driving device comprises:
 an advance mechanism, and
wherein the driving device is configured to apply a thrust force to the at least a part of the conveying device of the applicator.

17. The applicator assembly according to claim 16,
wherein the handle further comprises:
 a handheld device on which the advance mechanism is arranged; and
 a guide wire arranged on the handle,
 wherein the guide wire is configured to be coupled to the at least a part of the conveying device of the applicator, and
 wherein the guide wire is connected to the advance mechanism.

18. The applicator assembly according to claim 17,
wherein the handle has an elongated form, the receiving device being arranged on one end of the handle,
wherein the handle comprises:
 a guide wire duct,
 wherein the guide wire duct is configured to receive the guide wire, and
 wherein the guide wire duct extends through the handle in a longitudinal direction of the handle up to the application device.

19. The applicator assembly according to claim 14,
wherein a part of the receiving device comprises:
 a shielding, and
 wherein the shielding covers a part of the applicator received in the receiving device.

* * * * *